(12) United States Patent
Held et al.

(10) Patent No.: US 6,406,665 B1
(45) Date of Patent: Jun. 18, 2002

(54) TRANSESOPHAGEAL ECHO (TEE) PROBE DISINFECTION AND ELECTRICAL SAFETY TEST

(76) Inventors: Georg Held, Schloss Zeigenberg, Ober-Morlen (DE), 61239; Harald Raith, Flurstrasse 20, Tiefenbronn (DE), 75233

( * ) Notice: Subject to any disclaimer, the term of this patent is extended or adjusted under 35 U.S.C. 154(b) by 0 days.

(21) Appl. No.: 09/173,928

(22) Filed: Oct. 16, 1998

(30) Foreign Application Priority Data

Nov. 3, 1998 (EP) .............................. 97119135

(51) Int. Cl.$^7$ ................................. A61L 9/00
(52) U.S. Cl. ............... 422/28; 422/2; 422/105; 422/116; 422/300; 134/158; 210/103; 210/636
(58) Field of Search ............ 128/662.06, 660.08, 128/663.01; 134/158; 210/103, 636; 324/146; 422/105, 116, 300, 2, 28

(56) References Cited

U.S. PATENT DOCUMENTS

| 5,489,849 A | * | 2/1996 | Sadoway et al. ........... 324/446 |
| 5,558,841 A | | 9/1996 | Nakagawa et al. |
| 5,669,389 A | * | 9/1997 | Rotteveel ............... 128/662.06 |

FOREIGN PATENT DOCUMENTS

| DE | 3334999 A1 | 9/1983 |
| EP | 0038168 A1 | 4/1981 |
| FR | 2705896 A1 | 6/1993 |

* cited by examiner

Primary Examiner—Robert J. Warden, Sr.
Assistant Examiner—Imad Soubra

(57) ABSTRACT

An apparatus is described for disinfecting and testing the electrical safety of a transesophageal echo—TEE-probe. The apparatus comprises a receptacle adapted to receive the TEE-probe, apparatus for supplying the receptacle with a disinfection fluid and with a rinsing fluid, apparatus for removing any fluid from the receptacle, and an insulation tester having a first contact within the receptacle and a second contact connectable with the TEE-probe. The disinfecting and testing of the electrical safety is executed by supplying the receptacle with a disinfection fluid, disinfecting the TEE-probe, and removing the disinfection fluid. The receptacle is then supplied with a rinsing fluid and the TEE-probe is rinsed from remaining disinfection fluid. When the TEE-probe has been rinsed and before removing the rinsing fluid from the receptacle, an electrical safety test is executed with the TEE-probe by using the rinsing fluid.

15 Claims, 1 Drawing Sheet

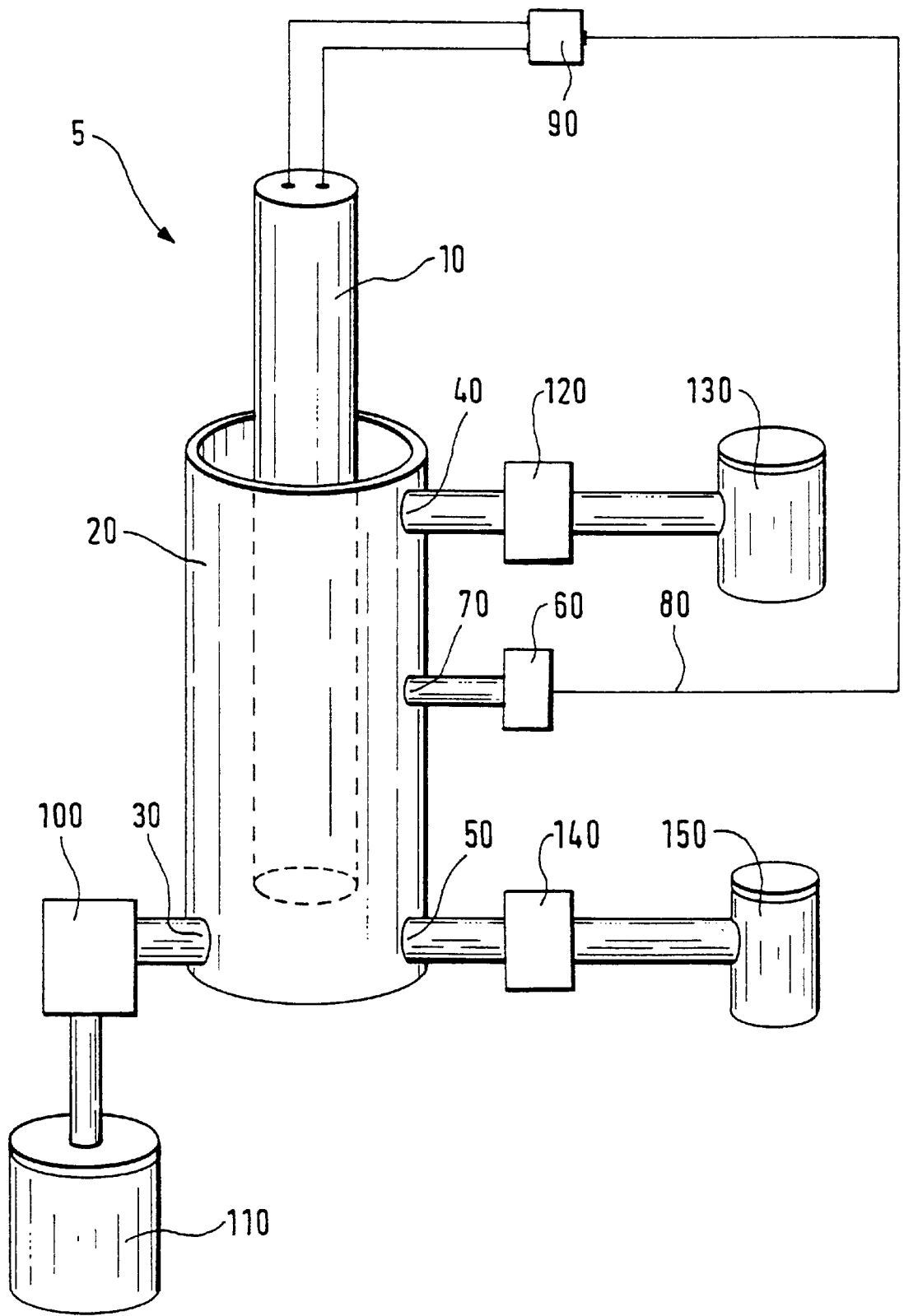

TRANSESOPHAGEAL ECHO (TEE) PROBE DISINFECTION AND ELECTRICAL SAFETY TEST

BACKGROUND OF THE INVENTION

The present invention generally relates to the disinfecting and testing the electrical safety of a transesophageal echo probe.

Transesophageal echo (TEE) cardiography is an established technique in the area of cardia imaging and involves the insertion of an ultrasound TEE probe into a subject's esophagus to scan the heart from inside the esophagus. An ultrasound TEE probe may be formed by modifying an endoscope, whereby an ultrasound transducer array is affixed to the distal end of the endoscope. Typically, the TEE probe is used with an ultrasound imaging system having electronics for remote excitation of the array to obtain cross-sectional images of the heart along a variety of scan planes as is well known.

Several TEE probes are described in the art, e.g., in "Transesophageal Cross-Section Echo cardiography With a Phased Array Transducer System" by Schluter et al., wherein an ultrasound TEE probe having a rotatable array is suggested for obtaining an improved assessment of left ventricular morphology, U.S. Pat. No. 4,543,960 to Harui et al. describing an ultrasound TEE probe having a rotatable array, U.S. Pat. No. 5,176,142 to Mason, or U.S. Pat. No. 5,176,142 to Fearnside et al.

Before an application, the TEE probe needs to be disinfected. The disinfection process is quite time consuming (generally 20 min up to 60 min) dependent on the respective disinfection fluid. In case that the TEE probe is kept in the disinfection fluid longer than needed, the life time of the TEE probe will strongly decrease.

Various cleaning apparatus for endoscopes are disclosed e.g. in EP-A-0038168, ER-A-2705896 and DE-A-3334999 U.S. Pat. No. 5,558,841 discloses a washing/sterilizing apparatus for an endoscope comprising a receptable adapted to receive the endoscope, means for supplying the receptable with a disinfection fluid, means for supplying the receptable with a rising fluid, and removing means for removing any fluid from the receptable.

Further more for the sake of patients' safety, it is important to perform an insulation test before using the TEE probe, such as IEC 601 or a test based thereon. The insulation test generally measures a leakage current between a reference potential and a shielding of the TEE probe. The shielding of the TEE probe normally mechanically surrounds and electrically shields the TEE probe and is coated with an insulating layer.

There is a lot of care, maintenance, and at least from time to time a safety check, necessary to keep the TEE probe working precisely and ensure a long lifetime. If the TEE probe is handled with the required care, an extended lifetime of up to 12 months can be achieved. It is desired to reduce high follow-up costs due to an early TEE probe exchange.

A disinfection and electrical test equipment for TEE probes is suggested in a technical information brochure of Svenska servicedepan, Malmo, Sweden. The disclosed TEE probe tester consists of a laminate board with two acrylic tubes, one for disinfection and one for rinsing, which must be mounted about 30 cm above the floor. The TEE probe tester is used to disinfect the TEE probe and at the same time to test the electrical safety, indicating whether the TEE probe needs to be tested for leakage by qualified technical personnel. For testing the electrical safety, the measuring part of the TEE probe tester uses the disinfection fluid available during the disinfection of the TEE probe as electrical contact medium. After disinfecting the TEE probe has to be removed from the TEE probe tester, inserted into a rinse tube, and rinsed off therein from the disinfection fluid. However, the disclosed TEE probe tester is not safe enough for clinical applications and does not provide a reliable disinfection and electrical testing.

NL-A-8800755 discloses an apparatus for sterilizing and testing the electrical safety of an ultrasonic probe for diagnostic purposes. The probe is inserted in a holder with a sterilizing fluid. Simultaneously to the sterilizing of the probe, an electrical leakage test of the probe is executed.

SUMMARY OF THE INVENTION

It is an object of the invention to provide an improved disinfection and electrical test equipment for TEE probes.

According to the invention, an apparatus for disinfecting and testing the electrical safety of a TEE probe comprises a receptacle adapted to receive the TEE probe, first supplying means for supplying the receptacle with a disinfection fluid, second supplying means for supplying the receptacle with a rinsing fluid, removing means for removing any fluid from the receptacle, and an insulation tester having a first contact within the receptacle and a second contact connectable with the TEE probe.

The disinfecting and testing of the electrical safety of the TEE probe is executed by supplying the receptacle with a disinfection fluid, disinfecting the TEE probe, and removing the disinfection fluid from the receptacle. The receptacle is then supplied with a rinsing fluid and the TEE probe is substantially rinsed from remaining disinfection fluid. When the TEE probe has been rinsed to a certain extent and before removing the rinsing fluid from the receptacle, an electrical safety test is executed with the TEE probe by using the rinsing fluid.

The TEE probe tester allows a reproducible and safe disinfection of the TEE probe and also ensures that the electrical requirements of the TEE probe are kept. The invention ensures a qualitative constant process in disinfection and thus the patients' safety for every application of the TEE probe. The TEE probe tester according to the invention also reduces the time required for the personnel to execute the disinfection process, and further extends the lifetime of the TEE probe due to the controlled execution of the disinfection process.

The TEE probe tester may be provided as a fully automatic device, so that all process steps are carried out automatically and do not require any manual aid.

In a preferred embodiment, a plurality of rinsing cycles is applied for cleaning the TEE probe, whereby either the same or different rinsing fluids may be used during each rinsing cycle and the rinsing might be exchanged between each rinsing cycle. In that case, the electrical safety test is preferably executed during a last rinsing cycle. This makes sure that the disinfecting fluid is removed and washed out to a maximum extent, so that the electrical safety test is carried out substantially in the pure rinsing-fluid. This allows a higher reproducibility and reliability of the results from the electrical safety test.

In another preferred embodiment, the conductance of the fluid in the receptacle is measured before executing the electrical safety test. This allows, e.g., to adapt measuring parameters of the electrical safety test to the determined conductance. This leads to an increased reliability of the measuring results since the conductance of the rinsing fluid might differ dependent on the quantity of remaining disinfectant, or on the different quality of the rinsing fluid, e.g., in case that tap water is used as rinsing fluid. Also, a further rinsing cycle might be initiated in case that the determined conductance lies beyond a predefined value, so that it can be expected that there is too much remaining disinfectant in the receptacle.

In another preferred embodiment, a self-test is executed, whereby the self-test is preferably carried out before each disinfection and insulation check, or dependent on the numbers of executed disinfections and insulation checks, or on a fixed time base.

In another preferred embodiment, a concentration of the disinfection fluid is determined and a disinfection time is set or can be set in accordance with the determined concentration. This supports a fully automated and reliable process.

BRIEF DESCRIPTION OF THE DRAWINGS

Other objects and many of the attendant advantages of the present invention will be readily appreciated and become better understood by reference to the following detailed description when considering in connection with the accompanied drawing:

FIG. 1 which shows a disinfection and electrical test equipment for TEE probes according to the invention.

DETAILED DESCRIPTION OF THE INVENTION

FIG. 1 shows a disinfection and electrical test equipment 5 for TEE probes according to the invention (referred to as TEE probe tester 5 hereafter). A TEE probe 10 is inserted in a receptacle 20, such as a tube, of the TEE probe tester. The receptacle 20 is provided with a first inlet 30 for supplying a disinfection fluid to the receptacle 20, a second inlet 40 for supplying a rinsing fluid to the receptacle 20, and a first outlet 50 for removing any fluid from the receptacle 20. The receptacle 20 is further coupled with an insulation tester 60 providing a first contact 70 within the receptacle 20 and a second contact 80 to be connected with an electrical shielding 90 of the TEE probe 10.

In a preferred embodiment, the first inlet 30 is coupled via a first controller 100 to a first tank 110 containing the disinfection fluid, the second inlet 40 is coupled via a second controller 120 to a second tank 130 containing the rinsing fluid, and the first outlet 50 is coupled via a third controller 140 to a third tank 150 for receiving the disinfection fluid and/or the rinsing fluid. In another embodiment, the third tank 150 will only receive the rinsing fluid, and the disinfection fluid is removed back into the first tank 110 and may be exchanged occasionally, e.g., after 10 days. The receptacle 20 may also comprise a fourth outlet coupled to a fourth tank for receiving the disinfection fluid after use. Preferably any inlet or outlet is arranged at a lower side of the receptacle 20. However, it is to be understood that all inlets and outlets can be coupled to other storing means as the tanks, e.g., a fluid system. In a further embodiment, the receptacle 20 is directly connected via the respective inlets and outlets with a regular water and disinfectant supply, e.g., of a hospital.

The disinfection fluid preferably is Aseptisol, Helipur H plus, Sekusept Extra N, Gigasept FF, or another equivalent disinfectant as known in the art. The rinsing fluid preferably is tap water and might comprise additives such as Micropur MT5, or another equivalent rinsing fluid as known in the art.

The controllers 100, 120, 140 are preferably embodied as pumps or valves and control the supply and/or removal of the fluid(s) to and/or from the receptacle 20. The controllers 100, 120, 140 may be controlled and coordinated by a central computer (not shown in FIG. 1) as known in the art.

In operation, the TEE probe 10 is placed in the receptacle 20 for executing the disinfection and insulation check. Before the TEE probe tester 5 starts the process, a self-test is executed. The self-test is preferably executed before each disinfection and insulation check, but can also be executed only from time to time dependent, e.g., on the numbers of executed disinfections and insulation checks or on a fixed time base. The self-test preferably checks the mechanical functionality of all mechanical parts associated with the inlets and outlets, such as the controllers 100, 120, 140. Further more, the self-test preferably checks the electrical functionality of the insulation tester 60 and other electrical parts of the TEE tester, such as electrical components of the controllers 100, 120, 140. An optional error indicator might indicate a failure determined or occurring during the self-test.

In a next step, the TEE probe tester 5 carries out the disinfection of the TEE probe 10. The receptacle 20 is filled with a disinfection fluid via the inlet 30. The TEE probe 10 is kept in the disinfection fluid for a predetermined period of time, preferably for 5 to 100 minutes, whereby the disinfection time depends on the used disinfection fluid. In a preferred embodiment, the disinfection time can be set to 15, 30 and 60 minutes. In another embodiment, the TEE probe tester 5 provides means for determining the concentration of the disinfection fluid and automatically sets the disinfection time in accordance with the determined concentration.

After disinfection, the TEE probe 10 needs to be cleaned from any remaining disinfection fluid, since most of the disinfection fluids are poisonous and aggressive, so that any remaining disinfection fluid can harm the patients. The disinfection fluid is removed from the receptacle 20, e.g., via the outlet 50 into a (waste) tank 150 or back into the tank 110. The receptacle 20 is filled or flushed with a rinsing fluid via the inlet 40 and the TEE probe 10 is thus rinsed off from the remaining disinfection fluid. The rinsing process can be repeated several times—as rinsing cycles—whereby either the same or different rinsing fluids can be applied for each rinsing cycle.

When the TEE probe 10 has been rinsed off to a certain extent, the insulation tester 60 executes an electrical safety test with the TEE probe 10. The first contact 70 of the insulation tester 60 is brought into contact with the rinsing fluid in the receptacle 20 and the second contact 80 thereof is connected with the electrical shielding 90 of the TEE probe 10. The impedance between the first 70 and the second 80 contact or other electrical parameters are determined and serve as a base for checking the electrical shielding 90 of the TEE probe 10. The insulation check preferably follows the IEC 601 guidelines or is based thereon.

The electrical safety test is preferably executed during a last rinsing cycle of a plurality of rinsing cycles, whereby the rinsing fluid is exchanged between each rinsing cycle.

In a preferred embodiment, the insulation tester 60 measures the conductance of the available rinsing fluid in the receptacle 20 before executing the electrical safety test, and adapts the measuring parameters, such as a measuring voltage, to the determined conductance. In case that the determined conductance lies beyond a predefined value, the TEE probe tester 5 of a further embodiment will indicate a signal and/or initiate a further rinsing cycle.

After the electrical safety test has been carried out, the rinsing fluid can be removed from the receptacle 20 and the TEE probe 10 is ready for a further application. However, the TEE probe 10 might also be kept within rinsing fluid in the receptacle 20.

We claim:

1. An apparatus for disinfecting and testing the electrical safety of a transesophageal echo—TEE-probe, comprising:

a receptacle adapted to receive the TEE-probe, first supplying means for supplying the receptacle with a disinfection fluid, second supplying means for supplying the receptacle with a rinsing fluid, removing means for removing any fluid from the receptacle, and an insulation tester having a first contact within the receptacle and a second contact connectable with the TEE-probe, whereby the insulation tester is adapted to execute an electrical safety test with the TEE-probe by using the rinsing fluid whereby the impedance of said probe is determined.

2. The apparatus according to claim 1, wherein the first supplying means comprises a first inlet coupled via a first controller to a first tank containing the disinfection fluid;

the second supplying means comprises a second inlet coupled via a second controller to a second tank containing the rinsing fluid; and the removing means comprises a first outlet coupled via a third controller to a third tank for receiving the disinfection fluid and/or the rinsing fluid.

3. The apparatus according to claim 1, wherein the first supplying means, the second supplying means and the removing means are arranged to couple at a lower side of the receptacle.

4. The apparatus according to claim 1, further comprising means for measuring the conductance of the fluid in the receptacle.

5. The apparatus according to claim 4, further comprising means for adapting measuring parameters to the determined conductance.

6. The apparatus according to claim 1, further comprising means for executing a self-test.

7. The apparatus according to claim 1, further comprising means for determining a concentration of the disinfection fluid and for setting a disinfection time in accordance with the determined concentration.

8. A method for disinfecting and testing the electrical safety of a transesophageal echo—TEE-probe in a receptacle adapted to receive the TEE-probe, comprising:

a first step of supplying the receptacle with a disinfection fluid, disinfecting the TEE-probe, and removing the disinfection fluid from the receptacle;

a second step of supplying the receptacle with a rinsing fluid and substantially rinsing the TEE-probe from remaining disinfection fluid; and when the TEE probe has been rinsed to a certain extent and before removing the rinsing fluid from the receptacle, a third step of executing an electrical safety test with the TEE-probe by using the rinsing fluid whereby the impedance of said probe is determined.

9. The method according to claim 8, wherein the second step comprises a step of applying a plurality of rinsing cycles, whereby either the same or different rinsing fluids are applied during each rinsing cycle.

10. The method according to claim 9, wherein the third step is executed during a last rinsing cycle of the plurality of rinsing cycles.

11. The method according to claim 8, further comprising a step, prior to the third step, of measuring the conductance of the fluid in the receptacle.

12. The method according to claim 11, further comprising a step of adapting measuring parameters to the determined conductance.

13. The method according to claim 11, further comprising a step of initiating a further rinsing cycle in case that the determined conductance lies beyond a predefined value.

14. The method according to claim 8, further comprising a step, prior to the first step, of executing a self-test before each disinfection and insulation check, dependent, on a number of executed disinfections and insulation checks or on a fixed time base.

15. The method according to claim 8, wherein the first step further comprises a step of determining a concentration of the disinfection fluid and a step of setting a disinfection time in accordance with the determined concentration.

* * * * *